US00PP33251P3

(12) United States Plant Patent
Karniel

(10) Patent No.: US PP33,251 P3
(45) Date of Patent: Jul. 13, 2021

(54) GRAPEVINE PLANT NAMED 'ARRATHIRYTHREE'

(50) Latin Name: *Vitis vinifera*
Varietal Denomination: ARRATHIRTYTHREE

(71) Applicant: AGRICULTURAL RESEARCH AND DEVELOPMENT LIMITED LIABILITY COMPANY, Bakersfield, CA (US)

(72) Inventor: Shachar Karniel, Bakersfield, CA (US)

(73) Assignee: Agricultural Research and Development Limited Liability Company, Bakersfield, CA (US)

( * ) Notice: Subject to any disclaimer, the term of this patent is extended or adjusted under 35 U.S.C. 154(b) by 0 days.

(21) Appl. No.: 16/602,173

(22) Filed: Aug. 20, 2019

(65) Prior Publication Data

US 2021/0059090 P1 Feb. 25, 2021

(51) Int. Cl.
*A01H 5/08* (2018.01)
*A01H 6/88* (2018.01)

(52) U.S. Cl.
USPC ..... Plt./207
CPC ..... *A01H 6/88* (2018.05)

(58) Field of Classification Search
USPC ..... Plt./207, 206, 205
CPC ..... A01H 5/0812
See application file for complete search history.

*Primary Examiner* — Kent L Bell
(74) *Attorney, Agent, or Firm* — Lewis Roca Rothgerber Christie LLP

(57) ABSTRACT

A new distinct variety of grapevine named 'ARRATHIRTYTHREE' abundantly forms attractive crisp seedless berries with a creamy yellow-green skin coloration; lax small-medium clusters which display a light muscat flavor. The fruit commonly is ready for harvesting during the end of June in San Joaquin Valley of Central California, U.S.A., and displays good eating qualities as a table grape. The fruit firmness renders the fruit well amenable for handling, shipping, and storage.

1 Drawing Sheet

Classification: The present invention relates to a new *Vitis vinifera* Grapevine.

Variety denomination: The new Grapevine has a varietal denomination 'ARRATHIRTYTHREE'.

BACKGROUND OF THE INVENTION

A breeding program was initiated during the late 90's near Bakersfield in San Joaquin Valley of Central California. In 2011, during this breeding program, a new variety of *Vitis vinifera* was created by deliberate cross breeding of two parent plants by emasculation of the pollen bearing organ of the maternal variety and introducing pollen from another variety: the paternal variety (i.e. the pollen parent). The maternal parent of the new variety was 11704/20, which is a very fertile creamy white table grape variety (non-patented in the United States). The paternal parent of the new variety was 11-25+4, a seedless white table grape with a natural sweet flavor (non-patented in the United States).

TABLE 1

'ARRATHIRTYTHREE' compared with parents & closely related variety:

| Variety/ Characteristic | 'ARRA THIRTYTHREE' | 11704/20 (Maternal) | 11 – 25 + 4 (Paternal) | Thompson Seedless |
|---|---|---|---|---|
| Capstem\ brush | medium\thin | thick\long | thick\ short | Short\ medium |

TABLE 1-continued

'ARRATHIRTYTHREE' compared with parents & closely related variety:

| Variety/ Characteristic | 'ARRA THIRTYTHREE' | 11704/20 (Maternal) | 11 – 25 + 4 (Paternal) | Thompson Seedless |
|---|---|---|---|---|
| Bunch density | lax | medium loose | lax | very tight |
| Flavor | light muscat | light muscat | natural | natural |

The parentage of the new variety can be summarized as follows:

11704/20 X 11-25+4

An artificial pollination was created, and the result was an embryo which possessed unique genetic qualities. The rudiments resulting from the above pollination were embryo rescued.

In 2012 the plant was transplanted to Bakersfield in San Joaquin Valley of Central California.

It was found that the new grapevine of the present invention possesses the following combination of characteristics:

(a) Forms attractive crisp seedless berries with a creamy yellow-green skin coloration; in lax small-medium clusters which display a light muscat flavor,
(b) Commonly bears fruit during the month of June in the San Joaquin Valley of Central California, U.S.A., and
(c) Bears fruit that is firm and is well amenable for storage, handling, and shipping.
(d) Produces 44 bunches per vine, and an average of about 2 bunches per shoot, at a total of 44 lbs. fruit per vine.

The new variety during observation to date has displayed no visible disease, and has displayed an ability to well resist cold, drought, heat; but sensitive to direct exposure to sun and wind. The fruit of the new variety has been found to display excellent handling and shipping qualities combined with desirable dessert eating qualities.

The new variety of the present invention has been found to undergo asexual propagation beginning in 2013 near Bakersfield in the San Joaquin Valley of Central California, U.S.A. by bud grafting on mature Thompson rootstock (non-patented in the United States). Such asexual propagation has been conducted thereafter in successive years to date and has shown that the characteristics of the new variety are strictly transmissible from one generation to another. Accordingly, the new variety undergoes asexual propagation in a true to type manner.

SUMMARY OF THE INVENTION

The new variety 'ARRATHIRTYTHREE' is a creamy yellow-green seedless table grape with a high production, e.g., about 44 bunches per vine, and an average of about 2 bunches per shoot.

Asexual reproduction by micro propagation of the new variety as performed near Bakersfield, Calif., U.S.A., shows that the forgoing and other distinguishing characteristics come true to form and are established and transmitted through succeeding propagations.

BRIEF DESCRIPTION OF THE DRAWINGS

The accompanying photographic illustration shows typical six-year-old specimens of the new variety, vegetatively propagated, in color as nearly true as it is reasonably possible to make in a color illustration of this character. Colors in the photograph may differ from the color values cited in the detailed botanical description below, which accurately describes the colors of the new Grapevine.

FIG. 1 shows leaves, stems and grapes of 'ARRATHIRTYTHREE'

DETAILED BOTANICAL DESCRIPTION

The chart used in the identification of colors is The R.H.S. Colour Chart of The ROYAL HORTICULTURAL SOCIETY (3rd Edition). The description is based on the observation of plants growing on 'Thompson Seedless' rootstock outdoors near San Joaquin Valley of Central California, U.S.A.

Vine characteristics:

*Vigor.*—Vigorous upright shoots.

*Productive capacity.*—Bearing at a natural, average capacity. Spur pruning. 44 bunches per vine, and an average of about 2 bunches per shoot, at a total of 44 lbs. fruit per vine.

*Trunk.*—Strong and developed. Diameter is 1.2" at 7" above ground. Rough with a fibrous, shaggy exterior. Light maple brown coloring RHS: greyed orange 166-D.

*First bloom in Bakersfield Calif.*—April 24th.

*Date of full bloom in Bakersfield Calif.*—April 29th.

*Date of bud burst in Bakersfield Calif.*—February 23rd.

Young shoot characteristics:

*Typical and observed entire shoot color.*—Yellow green 145A.

*Openness of tip.*—Wide open.

*Density of prostrate hairs on tip.*—Absent or very sparse.

*Anthocyanin coloration of prostrate hairs on tip.*—Yellow Green 144B.

*Density of erect hairs on tip.*—Absent or very sparse.

Young leaf characteristics:

*Color of upper side of blade.*—Yellow green 152A.

*Color of young leaf lower surface.*—Yellow Green 153A.

*Density of prostrate hairs between main veins on lower side of blade.*—Sparse.

*Density of erect hairs on main veins on lower side of blade.*—Absent or very sparse.

*Density of erect hairs between main veins on upper side of blade.*—Absent or very sparse.

*Density of prostrate hairs on main veins on lower side of blade.*—Absent or very sparse.

Shoot characteristics:

*Attitude (before tying).*—Semi-drooping.

*Color of dorsal side of internodes.*—Yellow green 145A.

*Color of ventral side of internodes.*—Yellow green 145B.

*Color of dorsal side of nodes.*—Yellow green 152A.

*Color of ventral side of nodes.*—Yellow green 152C.

*Density of erect hairs on internodes.*—Absent or very sparse.

*Density of prostrate hairs on internodes.*—Absent or very sparse.

*Length of tendrils (inches).*—6 inches, Diameter Of Tendrils: 0.7 inches.

*Color of tendrils.*—Yellow green 152C.

*Number of tendrils at bloom.*—Six.

*Position of first flowering and fruiting node.*—The first bunch is in the 3$^{rd}$ node.

*Inflorescence number per flowering shoot.*—6.

Flower characteristics:

*Reproductive organs.*—Fully developed stamens and fully developed gynoecium.

*Flower depth.*—0.1590 inches.

*Flower diameter.*—0.0955 inches.

*Pistil length.*—0.1160 inches.

*Pistol color.*—Green 143A.

*Pollen amount.*—Rich.

*Pollen color.*—Yellow 11C.

*Stamen color.*—Yellow green 144C.

*Stamen length (inches).*—0.16 inches.

*Number of stamen.*—6.

Mature leaf characteristics:

*Size of blade (inches).*—5.7×5.3.

*Shape of blade.*—The general overall shape of the blade is wedge-shaped.

*Blistering of upper side of blade.*—Absent or very sparse.

*Depth of upper lateral sinuses.*—Absent or very shallow.

*Number of lobes.*—Five.

*Arrangement of lobes of upper lateral sinuses.*—Closed.

*Arrangement of lobes of petiole sinus.*—Wide open.

*Length of teeth.*—Short.

*Ratio length/width of teeth.*—Medium.

*Shape of teeth.*—Mixture of both sides straight and both sides convex.

*Density of prostrate hairs between main veins on lower side of blade.*—Absent or very sparse.

*Density of erect hairs on main veins on lower side of blade.*—Absent or very sparse.
*Density of erect hairs between the main veins on the lower side of blade.*—Absent or very sparse.
*Density of prostrate hairs on main veins of the upper and lower sides of the blade.*—Absent or very sparse on both sides of blade.
*Length of petiole compared to length of middle vein.*—Much shorter.
*Main veins on upper side of blade.*—Yellow green 145B.
*Top side color.*—Green 137C.
*Bottom side color.*—Yellow green 144B.
*Texture of upper side of blade.*—Slightly rough.
*Texture of lower side of blade.*—Rough.
*Vein color on upper blade.*—Yellow green 145B.
*Vein color on lower blade.*—Yellow green 145C.
*Venation pattern for upper blade.*—Netlike venation.
*Venation pattern for lower blade.*—Netlike venation.
*Petiole length (inches).*—3.
*Petiole diameter (inches).*—0.08.
*Petiole color.*—Yellow green 146D.
*Petiole texture.*—Smooth.
*Base descriptors.*—Wedge shaped.
*Leaf margin.*—Crenate.
*Leaf apex.*—Cuspidate.
*Date of beginning of berry ripening in Bakersfield, Calif.*—June 26th.

Bunch characteristics:
*Size (peduncle excluded).*—Small-medium.
*Density of berries on bunch.*—Lax.
*Bunch length (inches).*—9.5".
*Bunch diameter (inches).*—6".
*Length of peduncle of primary bunch (inches).*—Long 2".
*Diameter of peduncle of primary bunch (inches).*—0.2".
*Peduncle of primary bunch color.*—Yellow-green 144A.
*Penducle texture.*—Smooth.
*Bunches per vine.*—44.
*Average bunch weight (lbs).*—1.

Berry characteristics:
*Size.*—Large.
*Length (inches).*—1.3.
*Weight (oz).*—0.2.
*Diameter (inches).*—0.8".
*Shape.*—Globose.
*Color of skin (without bloom).*—Yellow-green 154D.
*Flesh color.*—Yellow Green 145C.
*Brix.*—19.
*Titratable acidity percentage.*—1.53%.
*Juice.*—4.30 ph.
*Ease of detachment from pedicel.*—Moderately easy.
*Thickness of skin.*—Medium.
*Anthocyanin coloration of flesh.*—Absent or very weak.
*Firmness of flesh.*—Moderately firm.
*Particular flavor.*—Light muscat.
*Formation of seeds.*—None.
*Berries per bunch.*—85.

Pedicel characteristics:
*Length (inches).*—1.25.
*Diameter (inches).*—0.4.
*Color (inches).*—Yellow green 145B.
*Pedicel texture.*—Smooth.

Woody shoot characteristics:
*Main color.*—Dark brown.
*Woody shoot texture.*—Rough.
*Woody shoot color.*—Greyed Orange 165B.

Woody shoot measurements:
*Woody shoot length.*—4 foot and 3 inches.
*Diameter.*—0.24 inches.
*Internode length.*—2 inches.

Market use of observed plants: Fresh market.

Age and growing conditions: Six years growing under Y system in South Joaquin Valley (hot, dry summers).

Shipping characteristics:
*Number of days fruit has been stored under specific conditions.*—Fruit was in cold storage. Stored in poly bags inside Styrofoam boxes with sulfur pads. After 60 Days: rachises were 70% green rachis after 30 days cold storage green; 1% berry shattering after 30 days cold storage; no berry wrinkling or cracks were apparent.

DNA profile: To further characterize the new variety DNA was extracted from plant samples and a DNA profile was obtained in California USA using base pairs for 10 standard microsatellite DNA markers. The data is presented hereafter.

TABLE 2

DNA profile for 'ARRATHIRTYTHREE'

| Microsatellite DNA Marker | Allele Sizes in Base Pairs |
|---|---|
| M1 | 228, 236 |
| M2 | 239, 247 |
| M3 | 179, 185 |
| M4 | 212, 214 |
| M5 | 273, 273 |
| M6 | 133, 135 |
| M7 | 189, 191 |
| M8 | 251, 255 |
| M9 | 212, 214 |
| M10 | 237, 237 |

The 'ARRATHIRTYTHREE' variety has not been observed under all possible environmental conditions to date. Accordingly, it is possible that the phenotypic expression may vary somewhat with changes in light intensity and duration, cultural practices, and other environmental conditions.

Additional information relating to plant and fruit disease and pest resistance or susceptibility has not been observed to date. Resistance or susceptibility to specific plant and fruit diseases and pests has not been observed in the variety to date.

The plant hardiness zone and the heat/cold resistance has not been observed and are not known to date.

What is claimed is:

1. A new and distinct grapevine, botanically known as *Vitis vinifera*, identified as 'ARRATHIRTYTHREE', substantially as shown and described herein.

* * * * *

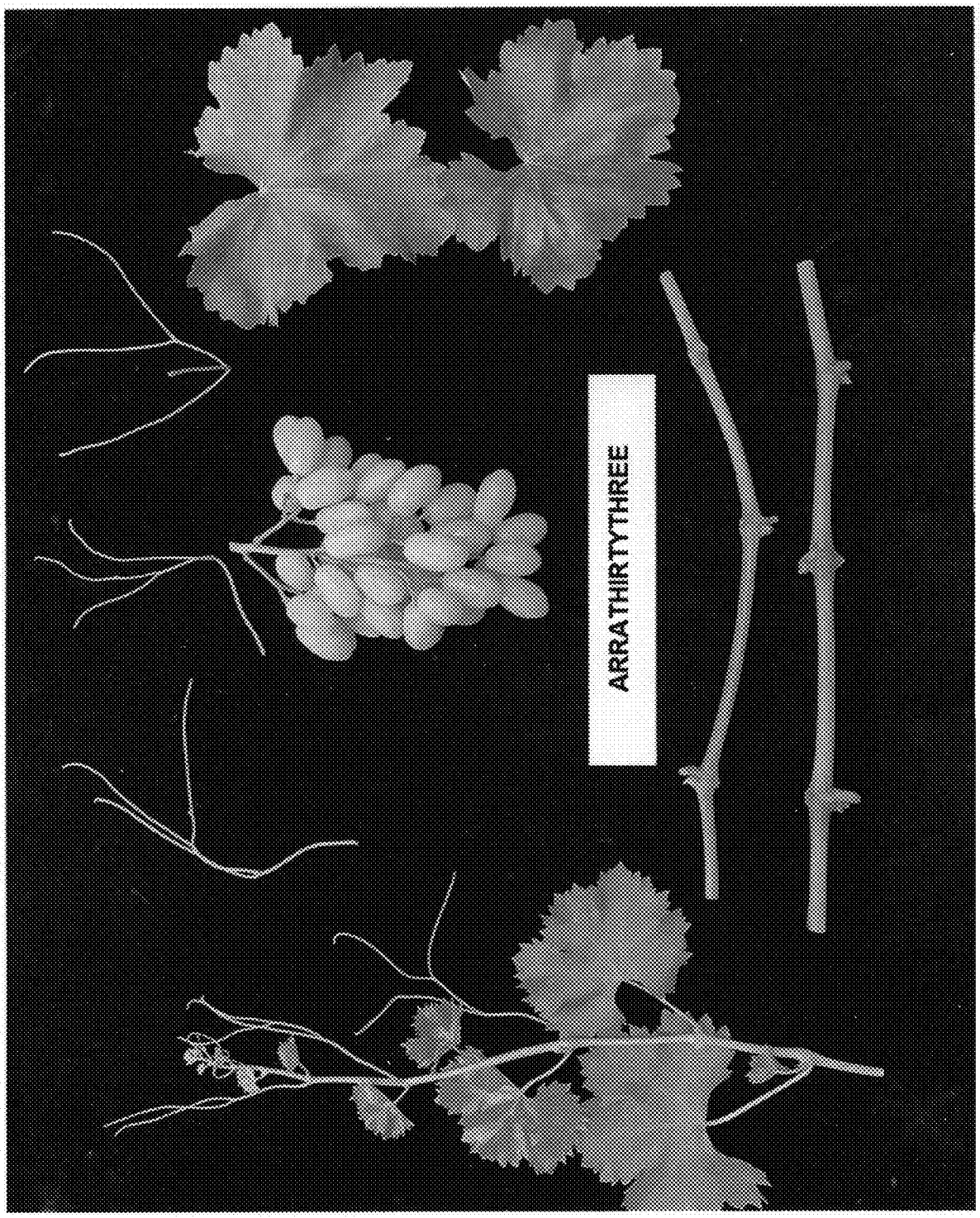
ARRATHIRTYTHREE